United States Patent [19]

Foley

[11] Patent Number: 4,468,451
[45] Date of Patent: Aug. 28, 1984

[54] PHOTOGRAPHIC PRODUCTS AND PROCESSES

[75] Inventor: James W. Foley, Andover, Mass.

[73] Assignee: Polaroid Corporation, Cambridge, Mass.

[21] Appl. No.: 500,415

[22] Filed: Jun. 2, 1983

[51] Int. Cl.$^3$ .................. G03C 1/40; G03C 5/54; G03C 1/10; G03C 7/00

[52] U.S. Cl. .................. 430/222; 430/241; 430/375; 430/445; 430/446; 430/405; 430/497; 430/542; 430/559; 430/564; 430/566; 430/611; 430/621; 430/623; 430/955; 430/958

[58] Field of Search ............ 430/222, 223, 542, 559, 430/375, 241, 405, 445, 446, 564, 566, 611, 623, 621, 497, 955, 958

[56] References Cited

U.S. PATENT DOCUMENTS

| 3,443,941 | 5/1969 | Rogers | 430/222 |
| 3,719,489 | 3/1973 | Cieciuch et al. | 430/222 |
| 4,098,783 | 7/1978 | Cieciuch et al. | 430/222 |
| 4,248,962 | 2/1981 | Lau | 430/559 |
| 4,358,525 | 11/1982 | Mooberry et al. | 430/222 |

Primary Examiner—Richard L. Schilling
Attorney, Agent, or Firm—Sybil A. Campbell

[57] ABSTRACT

This invention relates to photographic processes and products for forming an image in dye from a colorless precursor of a preformed image dye which is substituted with a moiety comprising a 1,3-sulfur-nitrogen group, said 1,3-sulfur-nitrogen group (a) being capable of undergoing cleavage in the presence of silver ion and/or soluble silver complex, and (b) possessing an amide substituent on the carbon atom in the 2-position that undergoes an intramolecularly accelerated cleavage reaction following the cleavage of said 1,3-sulfur-nitrogen group, which moiety maintains said precursor in its colorless form at least until the 1,3-sulfur-nitrogen group undergoes said cleavage. In a further embodiment, the cleavage of the amide substituent following the cleavage of the 1,3-sulfur-nitrogen group is used to provide an imagewise distribution of a photographically useful reagent, which reagent may be, for example, a photographically active reagent.

25 Claims, No Drawings

PHOTOGRAPHIC PRODUCTS AND PROCESSES

BACKGROUND OF THE INVENTION

1. Field of the Invention

This invention relates to the formation of dye images from a substantially colorless precursor of a preformed image dye. In another aspect, this invention relates to photographic products and processes for providing an imagewise distribution of a reagent such as a photographically active reagent or an image dye-providing moiety and to novel compounds useful therein.

2. Description of the Prior Art

U.S. Pat. No. 3,719,489 describes and claims photographic processes employing initially photographically inert compounds which are capable of undergoing cleavage in the presence of the imagewise distribution of silver ions made available during processing of a silver halide emulsion to liberate a reagent, such as, a photographically active reagent or a dye in an imagewise distribution corresponding to that of said silver ions. In one embodiment disclosed therein, color images are produced by using as the photographically inert compounds, color providing compounds which are substantially non-diffusible in the photographic processing composition but capable of undergoing cleavage in the presence of the imagewise distribution of silver ions and/or soluble silver complex made available in the undeveloped and partially developed areas of a silver halide emulsion as a function of development to liberate a more mobile and diffusible color-providing moiety in an imagewise distribution corresponding to the imagewise distribution of said ions and/or said complex. The subsequent formation of a color image is the result of the differential in diffusibility between the parent compound and liberated color-providing moiety whereby the imagewise distribution of the more diffusible color-providing moiety released in the undeveloped and partially developed areas is free to transfer.

Compounds disclosed as useful in liberating a reagent in the presence of said silver ions and/or silver complex are sulfur-nitrogen compounds containing the group

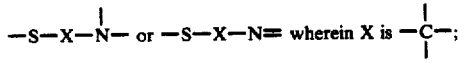

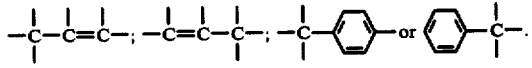

These 1,3-sulfur-nitrogen compounds may be linear or cyclic in structure, and in a particularly preferred embodiment are cyclic compounds, such as, thiazolidine compounds which comprise a dye radical having the chromophoric system of an azo, anthraquinone, phthalocyanine or other dye and a thiazolidin-2'-yl moiety which may be bonded directly to the dye radical or indirectly through an appropriate linking group.

Copending U.S. patent application Ser. No. 500,366 of Howard G. Rogers filed concurrently herewith is concerned with the formation of color images in a different manner using a different class of 1,3-sulfur-nitrogen compounds. Rather than relying on the differential in diffusibility between the colored parent compound and the liberated dye to form the color image, the ability of 1,3-sulfur-nitrogen compounds to undergo silver ion assisted cleavage is utilized to provide an imagewise distribution of a colored image dye from a substantially colorless precursor of a preformed image dye by employing a moiety comprising a 1,3-sulfur-nitrogen group to maintain said precursor in its substantially colorless form until said 1,3-sulfur-nitrogen group undergoes cleavage imagewise to correspond to the imagewise distribution of silver ion and/or soluble silver complex formed as a function of development of an imagewise exposed photosensitive element.

Copending U.S. application Ser. No. 500,391 of Roberta R. Arbree, James W. Foley and Frank A. Meneghini filed concurrently herewith also is concerned with forming dye images from a colorless precursor of a preformed image dye but employs a different class of compounds. As disclosed therein, the imagewise cleavage of a thiazolidinyl group is used to activate a β-elimination reaction, which β-elimination reaction provides the corresponding imagewise distribution of image dye from the colorless precursor compound.

The present invention is concerned with another class of 1,3-sulfur-nitrogen compounds and with their use in photographic products and processes.

SUMMARY OF THE INVENTION

According to the present invention, a new class of compounds is provided wherein the imagewise cleavage of 1,3-sulfur-nitrogen group is used to activate the intramolecular cleavage of an amide group for providing a corresponding imagewise distribution of a photographically useful reagent which may be colored, for example, an image dye, or colorless. In a preferred embodiment of the present invention, the intramolecular cleavage of the amide group following the silver ion assisted cleavage of the 1,3-sulfur-nitrogen group is utilized to provide an imagewise distribution of a colored image dye from a subtantially colorless precursor of a preformed image dye.

It is, therefore, one object of the present invention to provide photographic products and processes for forming a dye image from a colorless precursor of a preformed image dye which is substituted with a moiety comprising a 1,3-sulfur-nitrogen group, said 1,3-sulfur-nitrogen group (a) being capable of undergoing cleavage in the presence of silver ion and/or soluble silver complex, and (b) possessing an amide substituent on the carbon atom in the 2-position that undergoes an intramolecularly accelerated cleavage reaction following the cleavage of said 1,3-sulfur-nitrogen group, which moiety maintains said precursor in its colorless form at least until the 1,3-sulfur-nitrogen group undergoes said cleavage.

It is another object of the present invention to provide photographic products and processes for releasing an imagewise distribution of a photographically useful reagent by the intramolecularly accelerated cleavage of an amide group, preferably the cleavage of a carboxamido group, which occurs as a result of the imagewise cleavage of a 1,3-sulfur-nitrogen group.

It is a further object of the present invention to provide novel 1,3-sulfur-nitrogen compounds useful in the aforesaid photographic products and processes.

Other objects of the invention will in part be obvious and will in part appear hereinafter.

The invention accordingly comprises the processes involving the several steps and the relation and order of one or more of such steps with respect to each of the others, and the product and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DESCRIPTION OF THE PREFERRED EMBODIMENTS

In one aspect, the present invention is concerned with a photographic color process which provides a dye image, said process comprising photoexposing a photosensitive element containing a silver halide emulsion, said silver halide emulsion having associated therewith a colorless precursor of a preformed image dye; developing said exposed silver halide emulsion to form an image in developed silver and an imagewise distribution of silver ion and/or soluble silver complex in the partially developed and undeveloped areas of said emulsion; and forming as a function of said development a color image in dye from said colorless precursor, said colorless precursor of a preformed image dye being substituted with a moiety comprising a 1,3-sulfur-nitrogen group, said 1,3-sulfur-nitrogen group (a) being capable of undergoing cleavage in the presence of silver ion and/or soluble silver complex and (b) possessing an amide substituent on the carbon atom in the 2-position that undergoes an intramolecularly accelerated cleavage reaction following the cleavage of said 1,3-sulfur-nitrogen group, said moiety maintaining said precursor in its colorless form at least until said 1,3-sulfur-nitrogen group undergoes said cleavage. Preferably, the silver halide emulsion is a negative working emulsion and the color image is a positive image in dye.

The colorless image dye-providing compounds that may be employed in the above process may be represented by the formula (I) A—L—Z wherein A is a 1,3-sulfur-nitrogen group that undergoes cleavage in the presence of silver ion and/or soluble silver complex; L is an amide moiety capable of undergoing an intramolecularly accelerated cleavage reaction following the cleavage of said 1,3-sulfur-nitrogen group; and Z is a preformed image dye which taken with L is a colorless precursor of said preformed image dye, said A— being substituted on said precursor such that the precursor is maintained in its colorless form at least until said 1,3-sulfur-nitrogen group undergoes said cleavage.

The 1,3-sulfur-nitrogen group may be derived from the various compounds disclosed in aformentioned U.S. Pat. No. 3,719,489 including both the linear and cyclic compounds containing the grouping —S—X—N or —S—X—N= wherein X is 

Particularly preferred are the cyclic compounds where both the S and N atoms are included in the ring and especially the cyclic compounds illustrated in the following formula

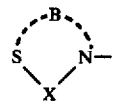

wherein B represents the atoms, preferably carbon atoms, necessary to complete a ring system containing at least 4 members and usually up to 20 members and X is $$-\overset{|}{\underset{|}{C}}-.$$

Examples of such compounds include thiazolidines, benzothiazolines and 1,2-tetrahydrothiazines.

As noted above, L is an amide moiety substituted in the 2-position of said 1,3-sulfur-nitrogen group that undergoes an intramolecularly accelerated cleavage reaction following the cleavage of said 1,3-sulfur-nitrogen group. As an illustration, a 1,3-sulfur group may be used to mask the α-keto group of an α-ketoamide, such as, a glyoxalamide to depress its hydrolysis rate and provide a masked compound that is substantially stable to alkaline hydrolysis until the 1,3-sulfur-nitrogen group undergoes cleavage in the presence of silver ion and/or soluble silver complex. A 1,3-sulfur-nitrogen group also may be used to mask the aldehyde group of a phthalaldehydamide to prevent the aldehyde group from assisting the hydrolysis of the neighboring carboxamido group until such time as the 1,3-sulfur-nitrogen group undergoes said silver ion assisted cleavage. It will be appreciated that any amide moiety may be used provided that the cleavage rate for the amide moiety taken with the silver assisted cleavage rate for the 1,3-sulfur-nitrogen group provides the image dye at a photographically useful rate for a given photographic system.

In addition to the specific embodiment described above, the compounds provided by the present invention may be used, generally, to release any of various photographically useful reagents in an imagewise fashion by employing the imagewise cleavage of a 1,3-sulfur-nitrogen group to activate the intramolecularly accelerated cleavage of an amide, which amide cleavage reaction releases the selected reagent. Compounds useful for this purpose may be represented by the formula (II) A—L—PHOTO wherein A is a 1,3-sulfur-nitrogen group capable of undergoing cleavage in the presence of silver ions and/or soluble silver complex; L is an amide moiety, preferably a carboxamido moiety capable of undergoing an intramolecularly accelerated cleavage reaction following the cleavage of said 1,3-sulfur-nitrogen group; and PHOTO is the radical of a photographically useful reagent selected from a photographically active reagent and a color-providing moiety selected from an image dye, an image dye intermediate and when taken with L is a colorless precursor of a preformed image dye, provided that when L—PHOTO is said colorless precursor, said A— is substituted on said precursor such that the precursor is maintained in its colorless form at least until said 1,3-sulfur-nitrogen group undergoes said cleavage.

In the foregoing formula, A is preferably a cyclic 1,3-sulfur-nitrogen group where both the S and N atoms are included in the ring and particularly, a 1,3-sulfur-nitrogen group of the formula

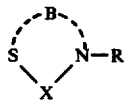

wherein B and X have the same meaning given above, particularly a thiazolidin-2'-yl group, and R is a monovalent hydrocarbon group, e.g., alkyl, aryl, alkaryl and aralkyl.

Examples of photographically active reagents that may be released imagewise from the inert parent compound include a development restrainer or arrestor, a silver halide solvent, a silver halide developing agent, an antifoggant, a gelatin hardener, an emulsion stabilizer, a toning agent, an anti-bronzing agent and so forth.

The image dye released including the dyes released from the colorless precursor compounds may comprise any of the general classes of dyes known in the art, for example, nitro, azo, xanthene and anthraquinone dyes; also leuco, indicator, temporarily "color shifted" and other dyes that take on a color change during or subsequent to processing to provide the ultimately desired color for the dye image via oxidation, changes in pH, alkaline hydrolysis of a blocking group, etc. It will be appreciated that such a color change is precluded without removal of the 1,3-sulfur-nitrogen group only in those compounds where L—PHOTO is the colorless precursor of a preformed image dye. Where the color-providing moiety is an image dye as distinguished from said colorless precursor or where it is a dye intermediate, A— or A—L— is used to provide, for example, an anchor and the dye image is formed as a result of the differential in diffusibility between the parent compound and the liberated color-providing moiety. Like the image dye released, the dye intermediate released may be any molecule as previously employed that reacts with another molecule to form a complete dye. For example, it may be a phenolic, naphtholic, methylene or other coupler and/or a molecule that reacts with a coupler, e.g., a quinonediimine or a carbonyl compound to form a complete dye.

Preferred compounds of the present invention may be represented by the formulae

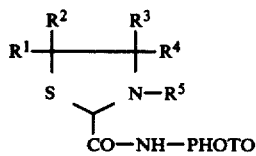

(A)

wherein $R^1$, $R^2$ and $R^3$ each are selected from hydrogen, alkyl, aryl, aralkyl and alkaryl; $R^4$ is selected from hydrogen, carboxy, N,N-dialkylcarboxamido, alkyl, aryl, aralkyl and alkaryl; $R^5$ is selected from alkyl, aryl, alkaryl and aralkyl; and PHOTO is the radical of a photographically useful reagent selected from a photographically active reagent and a color-providing moiety selected from an image dye, an image dye intermediate and when taken with said —CO—NH— is a colorless precursor of a preformed image dye; and

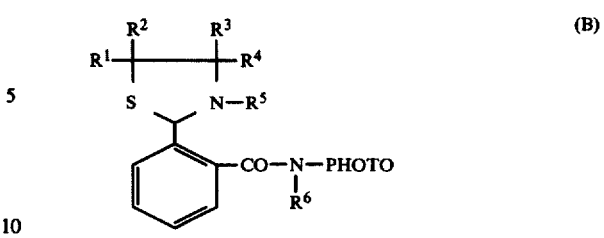

(B)

wherein $R^1$, $R^2$, $R^3$, $R^4$, and $R^5$ have the same meaning above; $R^6$ is alkyl or aryl; and PHOTO is the radical of a photographically useful reagent selected from a photographically active reagent and a color-providing moiety selected from an image dye, an image dye intermediate and when taken with said

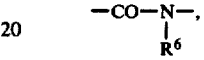

a colorless precursor of a preformed image dye.

Where PHOTO is taken with said amide group and is the colorless precursor of a preformed image dye, it may be, for example, a nitroaniline dye

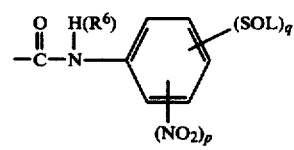

wherein $R^6$ has the same meaning given above, SOL is a solubilizing group, e.g., carboxy, hydroxy or sulfo; p is an integer 0 or 1; and q is an integer 0, 1 or 2; or an azo dye

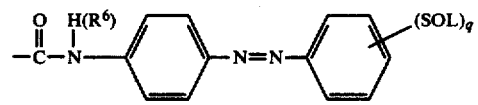

wherein $R^6$, SOL and q have the same meaning given above.

Typical aryl groups include phenyl and biphenyl and said alkyl groups comprising $R^1$, $R^2$, $R^3$, $R^4$, $R^5$ and $R^6$ usually contain 1 to 20 carbon atoms. Said aralkyl may be, for example, phenyl-substituted alkyl wherein said alkyl usually contains 1 to 20 carbon atoms, and said alkaryl may be, for example, alkyl-substituted phenyl wherein said alkyl usually contains 1 to 20 carbon atoms. The alkyl substituents of the N,N-dialkylcarboxamido group, the same or different, usually contain 1 to 6 carbon atoms.

It will be appreciated that the thiazolidinyl group and the moiety comprising the carboxamido group, like the radical of the photographic reagent, may be substituted with solubilizing groups, ballasting groups or other groups as may be appropriate for a given photographic system. Also, it will be appreciated that the moieties A and L may be derivatized to provide a photographically useful reagent in addition to that represented by PHOTO. For example, the compounds of formula B may be derivatized to release two image dyes, one dye being substituted on the phenyl group and the other being PHOTO, or to release an appropriately substituted aldehyde (or ketone) and also a coupler to react with the aldehyde (or ketone) to give a complete image dye.

The compounds of formulae A and B can be synthesized using conventional methods. For example, the compounds of formula A may be prepared by reacting a 2-carboxy-thiazolidine with ethyl chloroformate and reacting the resulting intermediate with the selected aniline, azo or other compound to give the desired product. The compounds of formula B can be prepared by reacting a thiazolidine-substituted benzoic acid with 1,1'-carbonyl-diimidazole to provide an intermediate which is reacted with the selected azo, aniline or other compound to give the desired product.

The following examples showing the preparation of compounds of the present invention are given for purposes of illustration and are not intended to be limiting.

EXAMPLE 1

Preparation of the compound having the formula

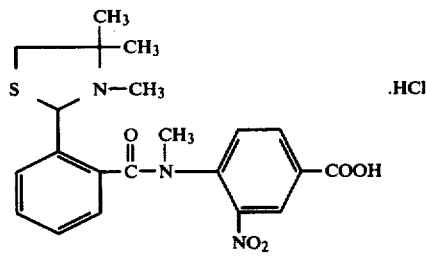

2-(2'-carboxyphenyl)-3,5,5-trimethyl-thiazolidine (6.00 g; 0.0239 mol) was mixed with 1,1'-carbonyl-diimidazole (3.88 g; 0.0239 mol) in 70 mls of dry N,N-dimethylformamide (DMF). Carbon dioxide evolution was observed. After stirring for one hour at room temperature, 4-carboxy-2-nitro-N-methylaniline (4.69 g; 0.0239 mol) was added providing an orange solution. Portion-wise addition of sodium hydroxide (50% oil dispersion, 3.44 g; 0.0717 mol) over a twenty minute period was accompanied by hydrogen evolution and an exotherm (to 50° C.). The resulting dark brown slurry was stirred at ambient temperature for fifteen minutes producing a dark brown gel. The mixture was kept overnight in the dark and under nitrogen. The mixture was acidified with dilute hydrochloric acid (14 ml conc. HCl in 130 ml of water), then adjusted to pH 4 with dilute aqueous sodium hydroxide. The mixture was filtered to give 2.7 g of an orange-yellow solid (the 2-nitro-4-carboxy-N-methylaniline reactant). The aqueous-DMF filtrate was saturated with sodium chloride and extracted with chloroform. A solid appeared (insoluble in both layers) which was filtered, washed with water and acetone. After drying, 1.96 g of the title compound was obtained as a cream powder; melting range 251.5°–253.5° C. (dec.). The dried (sodium sulfate) chloroform layer was evaporated to provide an orange oil which was triturated with 100 ml of ether. Solid appeared and was filtered off (1.57 g of the starting thiazolidine reactant). The ether filtrate was treated with HCl gas to precipitate 2.24 g of the mixed hydrochlorides of the starting thiazolidine reactant and of the title compound. Separation was achieved by dissolving the mixture in 15 ml of boiling methanol. After carbon treatment and filtration, ether (100 ml) was added to the methanolic solution along with some seed crystals of the title compound. In this manner an additional 0.81 g of the title compound was realized; melting point 255° C. (dec.); total yield 2.77 g (25% by weight).

Analysis for $C_2, H_{24}ClN_3O_5S$: Calculated: C, 54.1; H, 5.2; Cl, 7.6; N, 9.0; O, 17.2; S, 6.9; Found: C, 54.0; H, 5.3; Cl, 7.7; N, 8.9; O, 17.4; S, 6.7.

EXAMPLE 2

Preparation of the compound having the formula

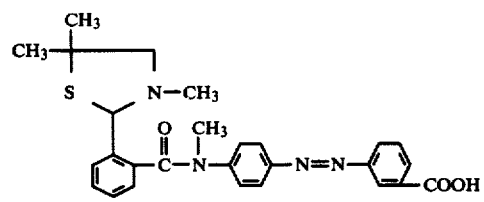

2.51 g of 2-(2'-carboxyphenyl)-3,5,5-trimethyl-thiazolidine and 1.62 g of 1,1'-carbonyldiimidazole were placed in a flask under a drying tube, and 15 ml of N,N-dimethylformamide were added at room temperature. The reaction mixture was stirred for 30 minutes giving the following intermediate designated A.

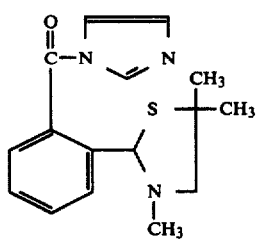

To this reaction mixture comprising the above intermediate was added 2.50 g of the azo compound designated B below.

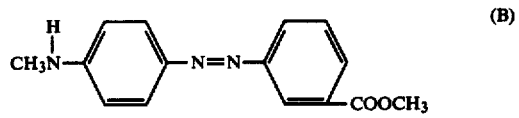

After stirring fifteen minutes, 0.50 g of a 50% oil dispersion of NaH was added in two portions. (The temperature rose slightly and foaming occurred.) The reaction mixture was stirred at room temperature for one hour and then at 60°–70° C. for two and one-half hours. After cooling to room temperature, the reaction mixture was poured into water, extracted 3x with ether and the ether extracts were washed with water, brine and dried. 200M of the following intermediate designated C were separated from the crude reaction mixture using preparative TLC techniques.

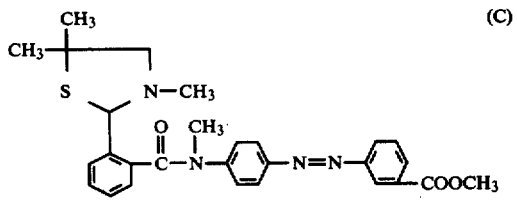

200 Mg of C was dissolved in methanol, and 7 ml of water containing potassium hydroxide was added to the methanol solution. The resulting mixture was milky, and additional methanol (about 10 ml) was added with stirring until the solution became a clear yellow. The solution was then heated to 60°-62° C. with stirring. After TLC showed the ester hydrolysis reaction complete, the reaction mixture was placed under aspirator vacuum for 10 minutes at 60° C. and then under a vacuum pump at about 50° C. When most of the methanol had been removed, a yellow oil precipitated. The oil was dissolved in about 30 ml of water and the solution extracted 3x with ether, adjusted to pH 5 and extracted 2x with ether. The ether extracts were combined, washed with brine and dried over sodium sulfate. The title compound was purified using preparative TLC techniques.

When a sample of the title compound was dissolved in 0.5 NaOH, the resulting solution appeared stable and visually to be almost colorless. Upon the addition of silver thiosulfate, a yellow color developed within 3 seconds, and after 15-30 seconds, the solution was an intense yellow.

The azo compound B employed in the above example was prepared as follows:

3-Aminobenzoic acid (27.4 g) was placed in about 350 ml of aqueous 85% lactic acid and cooled to −10° C. Sodium nitrite (14.0 g) was dissolved in a small amount of water and added slowly to the amino acid-lactic acid solution so that the temperature remained below 0° C. After this addition was complete, stirring was continued for 30 minutes at −10° C. and then at 0° C. to +5° C. for 15 minutes. The solution was then cooled to −10° C. and N-methylaniline (30.0 g) in about 200 ml of aqueous 85% lactic acid was slowly added. A light yellow precipitate formed. The reaction solution was stirred at 0° C. for one hour and at room temperature for two hours. (The reaction mixture became red-brown). It was then heated at 70° C. for two hours and allowed to stand overnight. The reaction mixture was diluted to 2 liters with water and filtered to collect a brown solid. The brown solid comprising the crude reaction product was treated with one liter of aqueous sodium bicarbonate at room temperature and stirred. The aqueous solution was washed with ether, acidified to pH 5 and a small amount of red precipitate was isolated. A large amount of the brown crude reaction product did not dissolve so the undissolved crude product was treated with sodium bicarbonate at 80° C. After filtering, extracting the filtrate with ether and acidifying to pH 5, an orange powder was obtained. The orange powder was dissolved in 500 ml of dry methanol. HCl gas was bubbled through the methanol solution for 20 minutes, and the solution was heated to 60° C. for one hour then allowed to stand overnight. It was poured into 3.5 liters of water, and the solid collected was washed with water, stirred 3x with hot sodium bicarbonate, then dissolved in chloroform. The chloroform solution was washed with sodium bicarbonate, dried over sodium sulfate and evaporated under vacuum to give 9 g of the title compound as an orange-red oil that solidified after drying at 90° C. under vacuum.

EXAMPLE 3

Preparation of the compound having the formula

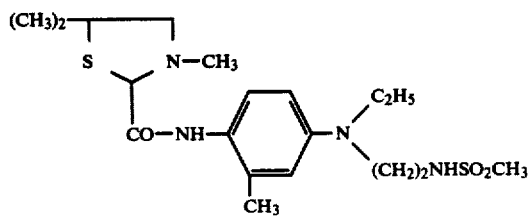

To 75 ml of chloroform was added 1.75 g of 2-carboxy-3,5,5-trimethyl-thiazolidine, and the mixture was stirred vigorously with cooling in a dry ice bath. To this was added 1.01 g of triethylamine and vigorous stirring was continued until all of the solids had dissolved. Then 1.08 g of ethylchloroformate was added in increments while maintaining the temperature between −10° C. to 0° C. The mixture was stirred in this temperature range for approximately 45 minutes. Then 3.07 g of 4-amino-3-methyl-N-ethyl-N-(2'-methylsulfonamido)ethylaniline.-hydrochloride in 50 ml of chloroform containing 1.01 g of triethylamine was added. The temperature was maintained below 0° C. for 30 minutes and then the mixture was allowed to come to room temperature overnight. The solvent was evaporated under reduced pressure to give an amber oil together with solids. This crude material was extracted with water to give a water insoluble oil and then the oil was dissolved in 200 mls of chloroform. The resulting amber colored chloroform solution was washed with two portions of water, dried over anhydrous magnesium sulfate, and evaporated under reduced pressure to give a light colored oil with a pale grey-green cast. The oil was dried in the presence of $P_2O_5$ to give a light colored tacky semi-solid. NMR of the solid indicated the presence of the title compound and possibly some solvent.

The hydrochloride salt of the title compound was prepared dissolving a sample of the above light amber, semi-solid product in 150 ml of chloroform and diluting this solution with 350 ml of ether. Hydrogen chloride gas was passed through the solution, and the white precipitate that formed was filtered, washed with fresh ether and dried under vacuum to give 3.1 g of white solid. Recrystallization from 25 ml of isopropanol followed by drying under vacuum gave 2.9 g of the hydrochloride salt (melting range: softens at about 108° C. then gradually decomposes).

EXAMPLE 4

Preparation of the compound having the formula

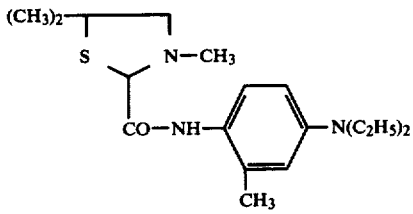

To 75 mls of pure dry chloroform was added 1.75 g of 2-carboxy-3,5,5-trimethyl thiazolidine and the resulting mixture was stirred vigorously while cooling in a dry ice bath. To the cold slurry was added 1.01 g of triethylamine and stirring was continued until the mixture was clear. The mixture was then cooled to approximately −5° C. and 1.08 g of ethylchloroformate was added in increments. The temperature was maintained below 0° C. and held between −10° C. and 0° C. for about one hour. To the cold solution was added 2.14 g of 4-amino-3-methyl-N,N-diethylaniline.hydrochloride dissolved in chloroform together with 1.01 g of triethylamine. A pink-red color formed but soon disappeared on further reaction. The reaction mixture was kept cold for one hour and then allowed to come to room temperature overnight. The reaction mixture, which was clear and light amber in color, was stirred at room temperature for another four and one-half hours and then evaporated to dryness under reduced pressure giving a tacky product. To this product was added 100 ml of petroleum ether, and the mixture was filtered to collect a grey, tacky material. This material was washed with fresh petroleum ether and pressed dry. 125 ml of cold water were added to give a grey tar. The water was decanted, and the tar was triturated with another 125 ml of fresh water. The mixture was filtered and the solids were washed with fresh water and dried under vacuum in the presence of $P_2O_5$ to give 1.2 g of the title compound as a pale white solid.

As noted previously, in one embodiment the present invention is concerned with the formation of a color image from certain colorless image dye-providing compounds comprising a colorless precursor of a preformed image dye. In this embodiment, the colorless compound may be present initially in the photosensitive element in a layer or layers other than the layer containing the light-sensitive silver halide emulsion, or it may be in the light-sensitive layer itself. For example, it may be in a layer on one side of the emulsion or in two layers, one on either side of the emulsion. If desired, it may be separated from the emulsion layer by one or more spacer layers. Where the colorless compound is present in the light-sensitive layer, the compound should be inert, that is photographically innocuous in that it does not adversely affect or impair image formation. If not photographically innocuous, the compound may be modified in a manner which does not interfere with the development process in any way, but which deactivates the compound so that it does not affect adversely the light-sensitive emulsion. Rather than being disposed in the photosensitive element, the colorless compound may be initially contained in a layer associated with an image-receiving layer in processes such as diffusion transfer processes where image-receiving elements are employed.

The formation of color images according to the subject invention is applicable to the preparation of both monochromatic and multicolor images. For example, the colorless image dye-providing compounds of this invention may be employed in photographic systems utilizing multilayer photosensitive elements comprising at least two selectively sensitive silver halide emulsion strata having said colorless image dye-providing compounds associated therewith which are processed simultaneously and without separation to provide a multicolor image. In such a structure, a barrier interlayer of silver complex scavenger, e.g., silver precipitant may be used, to confine diffusion of soluble silver complex to the appropriate stratum. Also, filter layers containing, e.g., bleachable filter dyes of the type described in U.S. Pat. Nos. 4,304,833, 4,358,118 and 4,304,834 may be used to control the spectral composition of light falling on the underlying light-sensitive layer. Another useful structure for obtaining multicolor images is the screen type negative described in U.S. Pat. No. 2,968,554 or that described in U.S. Pat. No. 3,019,124.

According to one method of forming color images, both the image dyes and their colorless parent compounds comprising the colorless precursor of a preformed image dye are substantially non-diffusible from their initial position in association with the photosensitive strata. To achieve the requisite non-diffusibility, the colorless parent compound may be appropriately substituted with an immobilizing group, e.g., a long chain alkyl group and the image dye released may be a dye that is substantially non-diffusible by nature or it may be rendered non-diffusible by appropriate substitution with an immobilizing group, by including a mordant in the same layer with said image dye or by other means that would prevent the dye from diffusing from the photosensitive element.

Though the developed silver present in the photosensitive element after image formation and any remaining silver halide may be removed in a conventional manner, for example, by a bleach-fix bath, it is preferred to bleach the developed silver and to complex residual silver halide in situ. In a particularly preferred embodiment, the silver halide emulsion employed is one which upon development contains low covering power silver in the developed areas whereby the need for bleaching is obviated. In these embodiments, it will be appreciated that the silver halide developing agents, the silver halide solvents and other reagents employed should be substantially non-staining.

Rather than forming monochromatic and multicolor images non-diffusible from the photosensitive element, it will be appreciated that the image dyes provided by the colorless parent compounds may be diffusible to form the color image on a single common image-receiving layer. In this embodiment, the subsequent formation of a color transfer image preferably employs a differential in diffusibility between the colorless parent compound and the liberated dye. This differential in diffusibility may be achieved in a known manner by the appropriate selection of an immobilizing group(s), such as a long chain alkyl or alkoxy group and/or solubilizing group(s), such as, hydroxy, carboxy or sulfo groups.

In the latter embodiments, where the image dyes released are diffusible, the photosensitive layer and the image-receiving layer may be in separate elements which are brought together during processing and thereafter retained together as the final print or separated following image formation, on the photosensitive and image-receiving layers may be in the same element. For example, the image-receiving layer may be coated on a support and the photosensitive layer coated on the surface of the image-receiving layer. The processing composition may be applied to the combined negative-positive element using a spreader sheet to facilitate spreading the liquid composition in a uniform layer adjacent the surface of the photosensitive layer. The image-receiving layer carrying the color image may be separated from the overlying photosensitive layer(s), e.g., with the aid of a stripping layer, or the color image may be viewed as a reflection print by employing a light-reflecting layer between the photosensitive and image-receiving layers.

Illustrative of still other film units are those where the negative and positive components together comprise a unitary structure and are laminated and/or otherwise physically retained together at least prior to image formation. Generally, such film units comprise a plurality of layers including a negative component comprising at least one light-sensitive layer, e.g., a silver halide layer and a positive component comprising an image-receiving layer which components are laminated together or otherwise secured together in physical juxtaposition as a single structure.

Included among such structures are those adapted for forming a transfer image viewable without separation, i.e., wherein the positive component containing the transfer image need not be separated from the negative component for viewing purposes. In addition to the aforementioned layers, such film units include means for providing a reflecting layer between the image-receiving and negative components in order to mask effectively the silver image or images formed as a function of development of the silver halide layer or layers and also to provide a background for viewing the transfer image in the receiving component, without separation, by reflected light. This reflecting layer may comprise a preformed layer of a reflecting agent included in the film unit or the reflecting agent may be provided subsequent to photoexposure, e.g., by including the reflecting agent in the processing composition.

The aforementioned layers are preferably carried on a support and preferably are employed with another support positioned on the opposed surface of the layers carried by the first support so that the layers are sandwiched or confined between the support members, at least one of which is transparent to permit viewing of the final image. Such film units usually are employed in conjunction with means, such as, a rupturable container containing the requisite processing composition and adapted upon application of pressure of applying its contents to develop the exposed film unit. Film units of this type are now well known and are described, for example, in U.S. Pat. Nos. 3,415,644, 3,415,645, 3,415,646, 3,594,164 and 3,594,165.

The processing composition employed comprises an aqueous solution and usually, an aqueous alkaline solution of a silver halide developing agent and a silver halide solvent. The named ingredients may be present initially in the aqueous medium or may be present initially in the photographic film unit, for example, in the emulsion and/or image-receiving and/or spacer layers as heretofore suggested in the art. When such ingredients are present initially in the film unit, the processing composition is formed by contacting the product with a suitable aqueous medium to form a solution of these ingredients.

The alkali employed may be any of the alkaline materials heretofore employed, such as sodium or potassium hydroxide and like the developing agent and the solvent may be initially in a layer or layers of the film unit.

The silver halide solvent also may be any of the heretofore known materials, such as sodium or potassium thiosulfate, sodium thiocyanate or uracil; also the thioether-substituted uracils, pseudo-uracils and other compounds disclosed and claimed in U.S. Pat. No. 4,126,459; the 1,3-disulfonylalkanes and cycloalkanes of U.S. Pat. Nos. 3,769,014 and 3,958,992, respectively; or the alkanes containing an intralinear sulfonyl group and, e.g., an intralinear N-tosylsulfimido or N-tosylsulfoximido group as disclosed and claimed in U.S. Pat. No. 4,107,176. Also, a silver halide solvent precursor may be used such as those disclosed in U.S. Pat. No. 3,698,898 and as disclosed and claimed in copending U.S. patent application Ser. No. 382,479 filed May 27, 1982.

Examples of silver halide developing agents that may be employed are hydroquinone and substituted hydroquinones, such as tertiary butyl hydroquinone, 2,5-dimethyl hydroquinone, methoxyhydroquinone, ethoxyhydroquinone, 4'-methylphenylhydroquinone; pyrogallol and catechols, such as catechol, 4-phenyl catechol and tertiary butyl catechol; aminophenols, such as 2,4,6-diamino-orthocresol; 1,4-diaminobenzenes, such as p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid and other enediols, such as, tetramethyl reductic acid; hydroxylamines, such as N,N-di-(2-ethoxyethyl)hydroxylamine, N,N-di-(2-methoxyethyl)hydroxylamine and N,N-di-(2-methoxyethoxyethyl)hydroxylamine; and heterocyclic compounds, such as, 1-phenyl-3-pryazolidone and 4-methyl-4-hydroxymethyl-1-phenyl-3-pyrazolidone.

Usually, though not necessarily, the processing composition includes a viscosity-increasing reagent such as a cellulosic polymer, e.g., sodium carboxymethyl cellulose, hydroxyethyl cellulose, carboxymethyl hydroxyethyl cellulose, etc; an oxime polymer, e.g., polydiacetone acrylamine oxime; or other high molecular weight polymers.

In addition to the aforementioned ingredients, the processing composition also may contain antifoggants, preservatives and other materials as conventionally used in the art.

The processing composition may be applied to the photosensitive element, for example, by coating, dipping, spraying or by the use of a rupturable container or pod such as disclosed in U.S. Pat. No. 2,543,181, the container being positioned in the film unit so as to be capable upon rupturing of spreading its contents in a substantially uniform layer.

The photosensitive element may be any of those conventionally employed and generally comprises a silver halide emulsion carried on a base, for example, glass, paper or plastic film, such as cellulose triacetate film, polyethylene terephthalate film, polystyrene film and polyolefin films, e.g, polyethylene and polypropylene films. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

Depending upon the particular photographic system, a mordant for the dye image may be used in association with the photosensitive layers as discussed above, or a separate image-receiving element may be employed. The image-receiving layer, i.e., dyeable stratum may comprise any of the materials known in the art, such as polyvinyl alcohol, gelatin, etc., preferably containing a mordant for the transferred image dye(s). The dyeable stratum can be in the same element as the photosensitive layer or it may be in a separate element as appropriate for a given photographic process.

In diffusion transfer processes employing an aqueous alkaline processing composition, it is well known to employ an acid-reacting reagent in a layer of the film unit to lower the environmental pH following substantial dye transfer in order to increase the image stability. For example, the previously mentioned U.S. Pat. No. 3,415,644 discloses systems wherein the desired pH reduction may be effected by providing an acid-reacting layer adjacent the dyeable stratum. These layers may comprise polymers which contain acid groups, e.g, carboxylic acid and sulfonic acid groups, which are capable of forming salts with alkali metals or with organic bases; or potentially acid-yielding groups such as anhydrides or lactones. Preferably the acid polymer contains free carboxyl groups. Alternatively, the acid-reacting reagent may be in a layer adjacent to the silver halide most distant from the image-receiving layer. Another system for providing an acid-reacting reagent is disclosed in U.S. Pat. No. 3,576,625.

An inert interlayer or spacer layer may be disposed between the polymeric acid layer and the dyeable stratum in order to control or "time" the pH reduction so that it is not premature and interferes with the development process. Suitable spacer or "timing" layers for this purpose are described with particularity in U.S. Pat. Nos. 3,362,819; 3,419,389; 3,421,893; 3,455,686; and 3,575,701.

The acid-reacting layer and associated spacer layer are usually contained in the image-receiving element in systems wherein the dyeable stratum and photosensitive strata are contained on separate supports, e.g., between the support for the receiving element and the dyeable stratum. In integral film units, these layers may be associated with the dyeable stratum, e.g., on the side of the dyeable stratum opposed from the photosensitive element or, if desired, they may be associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing composition.

In addition to the aforementioned layers, the film units may contain additional layers as commonly used in the art, such as a layer of antihalation dye, and/or a layer of filter dye arranged between differentially color-sensitive emulsion layers. Depending upon the particular photographic system, it may be desirable to use antihalation and filter dyes which become decolorized during photographic processing.

It will be understood that in the other embodiments of the present invention where the parent compound releases, for example, a photographically active reagent, the parent compound may be disposed either in the photosensitive element or in a second element depending upon the particular photographic system and the photographic reagent to be released. The parent compound and the reagent released can have the same or different mobility characteristics as may be required for a given process. As discussed above, the respective mobilizing characteristics can be adjusted in a known manner by appropriate substitution with immobilizing and/or solubilizing groups. Depending upon the particular parent compound, it may be advantageous to employ a combination of immobilizing and solubilizing groups to render the compound non-diffusible yet more wettable in the processing composition. Where it is desired to release, for example, a diffusible dye from a colored substantially non-diffusible parent compound anchored with a single immobilizing group, the anchor should be positioned on the parent compound such that upon cleavage, it will be on a fragment different from the fragment released as the diffusible color-providing moiety. Also, it may be preferable to position the immobilizing group on that portion of the parent compound that ultimately forms a complex with the silver ion upon cleavage.

The following examples are given to illustrate the formation of an imagewise distribution of a photographic reagent in accordance with the present invention and are not intended to be limiting.

EXAMPLE I

A photosensitive element was prepared by coating a gelatin coated transparent polyester film base with the following layers:

1. a layer of the compound of Example 3 dispersed in gelatin and coated at a coverage of 100 mgs/ft$^2$ of gelatin and 200 mgs/ft$^2$ of said compound of Example 3 having the formula

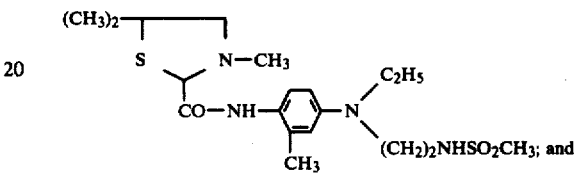

2. a gelatino silver iodobromide emulsion coated at a coverage of 100 mgs/ft$^2$ silver.

A second element was prepared by coating a transparent polyester film base with a polymeric acid layer, a timing layer and a layer of 25 mgs/ft$^2$ benzoyl peroxide and 50 mgs/ft$^2$ of naphthol coupler in a matrix of 25 mgs/ft$^2$ of a medium molecular weight copolymer of 82% vinylacetate and 18% vinylalcohol. The naphthol coupler had the formula

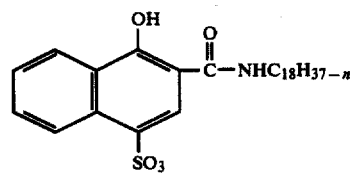

The photosensitive element was exposed imagewise, superposed with said second element and processing was carried out by spreading an aqueous alkaline processing composition between the superposed elements at a gap of approximately 0.001 inch. The processing composition comprised an aqueous solution containing, by weight, 4% medium molecular weight carboxymethylcellulose, 6.1% sodium hydroxide, 2.1% lithium hydroxide, 0.5% Metol and 1.0% sodium thiosulfate. After an imbibition time of about two minutes in the dark, the respective elements were separated to reveal a cyan image in said second element.

EXAMPLE II

A photosensitive element was prepared by coating a transparent gel subcoated polyester film base with the following layers:

1. a layer of the hydrochloride salt of the compound of Example 1 coated at a coverage of 90 mgs/ft$^2$ in gelatin, said hydrochloride salt having the formula

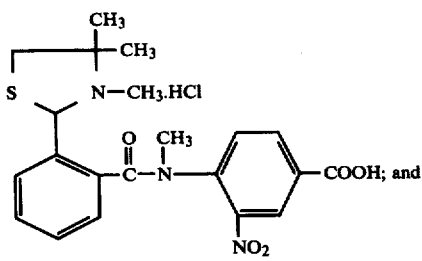

2. a gelatino silver iodobromide emulsion coated at a coverage of 50–60 mgs/ftr² silver.

The photosensitive element was exposed imagewise and processed against an image-receiving element comprising a layer of dyeable film-forming material coated on a baryta paper base at a gap of 0.0030 inch using an aqueous alkaline processing composition containing the following in % by weight:

| | |
|---|---|
| Carboxymethyl cellulose | 4.2 |
| Sodium hydroxide | 2.4 |
| Sodium sulfite | 2.0 |
| Sodium thiosulfate | 0.5 |
| Tetramethylreductic acid | 1.0 |
| and water to make 100% | |

After an imbibition time of three minutes in the dark, the respective elements were separated to show a positive yellow dye image.

The solution kinetics of the hydrochloride salt of the compound of Example 1 also were studied in aqueous alkaline solution in the presence and in the absence of soluble silver complex. It was found that this compound hydrolyzed with a $T\frac{1}{2}=24$ seconds in the presence of soluble silver (0.8M of NaOH, $10^{-3}$M Ag(S$_2$O$_3$)$_2$, $10^{-5}$M Ex. 1, HCl salt; 25° C.) and hydrolyzed with a $T\frac{1}{2}=115$ hours in the absence of soluble silver (1.0N aq. NaOH, $10^{-5}$M Ex. 1, HCl salt; 25° C.).

The solution kinetics of the compound of Example 2 also were studied. This compound was nearly colorless in solution and when treated with alkaline silver thiosulfate gave yellow azo dye. The azo dye formed with a $T\frac{1}{2}=32$ hours in the absence of soluble silver (0.5N aq. NaOH, $5\times10^{-5}$M Ex. 2; 25° C.) and with a $T\frac{1}{2}=11$ seconds in the presence of soluble silver (0.5N aq. NaOH, $10^{-3}$M Ag(S$_2$O$_3$)$_2$, $5\times10^{-5}$M; 25° C.). A plot of the optical density versus time for azo dye formation gave an "S" shaped curve, typical of an $A^{T\frac{1}{2}a}B^{T\frac{1}{2}b}C$ reaction, from which values of $T\frac{1}{2}^a=1$ to 3 seconds and $T\frac{1}{2}^b=10$ seconds could be estimated.

It will be appreciated that the photographic systems of the present invention for providing an imagewise distribution of a photographic reagent may be used to provide dyes, dye intermediates and photographic reagents other than those specifically mentioned. Also, it will be appreciated that the present systems may be used with film structures other than those illustrated.

Since certain changes may be made in the herein-defined subject matter without departing from the scope of the invention herein involved, it is intended that all matter contained in the above description should be interpreted as illustrative and not in a limiting sense.

What is claimed is:

1. A photographic color process which provides a dye image, said process comprising photoexposing a photosensitive element containing a silver halide emulsion, said silver halide emulsion having associated therewith a colorless precursor of a preformed image dye; developing said exposed silver halide emulsion to form an image in developed silver and an imagewise distribution of silver ions and/or soluble silver complex in the partially developed and undeveloped areas of said emulsion; and forming as a function of said development a color image in dye from said colorless precursor, said colorless precursor of a preformed image dye being substituted with a moiety containing a 1,3-sulfur-nitrogen group, said 1,3-sulfur-nitrogen group (a) being capable of undergoing cleavage in the presence of said silver ions and/or soluble silver complex and (b) possessing an amide substituent on the carbon atom in the 2-position which upon cleavage of said 1,3-sulfur-nitrogen group, undergoes an intramolecularly accelerated cleavage reaction, said moiety maintaining said precursor in its colorless form at least until said 1,3-sulfur-nitrogen group undergoes said cleavage.

2. A process as defined in claim 1 wherein said image dye is substantially non-diffusible from the layer in which it is positioned during said photoexposure.

3. A process as defined in claim 1 wherein said colorless precursor is substantially non-diffusible from the layer in which it is positioned during said photoexposure.

4. A process as defined in claim 3 wherein said colorless precursor is positioned in said silver halide emulsion during photoexposure.

5. A process as defined in claim 1 wherein said image dye provided by said colorless precursor is diffusible, said process including the step of transferring said diffusible image dye to an image-receiving layer in superposed relationship with said silver halide emulsion.

6. A process as defined in claim 5 wherein a light-reflecting layer is provided between said silver halide emulsion and said image-receiving layer, whereby said dye image may be viewed against said light-reflecting layer, said light-reflecting layer being effective to mask said developed silver halide emulsion from one viewing said dye image.

7. A process as defined in claim 1 wherein said silver halide emulsion is a negative working silver halide emulsion whereby a positive color image is formed as a function of said development.

8. A process as defined in claim 1 wherein said substituent in the 2-position of said 1,3-sulfur-nitrogen group is a carboxamido substituent.

9. A photographic product comprising a photosensitive element comprising a plurality of layers including a support; a silver halide emulsion in a layer on said support; and in a layer on the same side of said support as said silver halide emulsion, a colorless precursor of a preformed image dye substituted with a moiety containing a 1,3-sulfur-nitrogen group, said 1,3-sulfur-nitrogen group (a) being capable of undergoing cleavage in the presence of silver ions and/or soluble silver complex and (b) possessing an amide substituent on the carbon atom in the 2-position which upon cleavage of said 1,3-sulfur-nitrogen group undergoes an intramolecularly accelerated cleavage reaction, said moiety maintaining said precursor in its colorless form at least until said 1,3-sulfur-nitrogen group undergoes said cleavage.

10. A photographic product as defined in claim 9 wherein said colorless precursor is non-diffusible in aqueous alkaline solution.

11. A photographic product as defined in claim 9 wherein said image dye provided by said colorless precursor is non-diffusible in aqueous alkaline solution.

12. A photographic product as defined in claim 9 wherein said image dye provided by said colorless precursor is diffusible in aqueous alkaline solution and said product includes an image-receiving layer so positioned so to be capable of receiving by diffusion said imagewise distribution of said diffusible dye.

13. A photographic product as defined in claim 12 which additionally includes means for applying an aqueous processing composition to provide an aqueous alkaline solution of a silver halide developing and a silver halide solvent.

14. A photographic product as defined in claim 12 which includes a light-reflecting layer between said silver halide emulsion and said image-receiving layer, whereby said dye image formed by said imagewise distribution of diffusible dye may be viewed by reflection, said light-reflecting layer being effective to mask said developed silver halide emulsion from one viewing said dye image.

15. A photographic product as defined in claim 9 wherein said colorless precursor is positioned in said silver halide emulsion.

16. A photographic product as defined in claim 9 which includes a silver halide developing agent in said silver halide emulsion layer.

17. A photographic product as defined in claim 16 which includes a silver halide solvent in a layer on the same side of the support as said silver halide emulsion.

18. A photographic product as defined in claim 9 wherein said silver halide emulsion is a negative working emulsion.

19. A photographic product as defined in claim 9 which additionally includes an acid-reacting layer.

20. A photographic product as defined in claim 9 wherein said substituent in the 2-position of said 1,3-sulfur-nitrogen group is a carboxamido substituent.

21. A photographic process for providing an imagewise distribution of a photographically useful reagent, which process includes the steps of developing a photosensitive element comprising an exposed silver halide emulsion with an aqueous alkaline processing composition; forming in partially developed and in undeveloped areas an imagewise distribution of silver ions and/or soluble silver complex; contacting said imagewise ditribution of silver ions and/or soluble silver complex with a compound comprising the radical of a photographically useful reagent substituted with a moiety containing a 1,3-sulfur-nitrogen group, said 1,3-sulfur-nitrogen group (a) being capable of undergoing cleavage in the presence of said silver ions and/or soluble silver complex and (b) possessing an amide substituent on the carbon atom in the 2-position which upon cleavage of said thiazolidinyl group undergoes an intramolecularly accelerated cleavage reaction; and forming as a function of contacting said imagewise distribution of said silver ions and/or soluble silver complex with said compound, a corresponding imagewise distribution of said photographically useful reagent.

22. A photographic product as defined in claim 21 wherein said substituent in the 2-position of said 1,3-sulfur-nitrogen group is a carboxamido substituent.

23. A photographic product as defined in claim 22 wherein said 1,3-sulfur-nitrogen group is a thiazolidin-2-yl group.

24. A photographic product comprising a photosensitive element comprising a plurality of layers including a support; a silver halide emulsion in a layer on said support; and in a layer on the same side of said support as said silver halide emulsion, a compound comprising the radical of a photographically useful reagent substituted with a moiety containing a 1,3-sulfur-nitrogen group, said 1,3-sulfur-nitrogen group (a) being capable of undergoing cleavage in the presence of silver ions and/or soluble silver complex and (b) possessing an amide substituent on the carbon atom in the 2-position which upon cleavage of said 1,3-sulfur-nitrogen group undergoes an intramolecularly accelerated cleavage reation to provide said photographically useful reagent.

25. A photographic product comprising first and second sheetlike elements, said first element comprising a plurality of layers including a support; a photosensitive silver halide emulsion in a layer on said support; in a layer in one of said first and second sheetlike elements, a compound comprising the radical of a photographically useful reagent substituted with a moiety containing a 1,3-sulfur-nitrogen group, said 1,3-sulfur-nitrogen group (a) being capable of undergoing cleavage in the presence of silver ions and/or soluble silver complex and (b) possessing an amide substituent on the carbon atom in the 2-position which upon cleavage of said 1,3-sulfurnitrogen group, undergoes an intramolecularly accelerated cleavage reaction to provide said photographically useful reagent; and means for applying an aqueous alkaline processing composition to provide a silver halide developing agent and a silver halide solvent in a substantially uniform layer between said emulsion layer and said second sheetlike element in superposed relationship therewith.

* * * * *